United States Patent
Brugger et al.

[11] Patent Number: 5,928,177
[45] Date of Patent: Jul. 27, 1999

[54] TECHNIQUE FOR LOADING A PUMP HEADER WITHIN A PERISTALTIC PUMP OF A DIALYSIS MACHINE

[75] Inventors: James Brugger, Newburyport, Mass.; Dan Lee Hendrickson, Golden, Colo.; Jeff Burbank, Boxford, Mass.

[73] Assignee: COBE Laboratories, Inc., Lakewood, Colo.

[21] Appl. No.: 08/712,488

[22] Filed: Sep. 11, 1996

Related U.S. Application Data

[60] Provisional application No. 60/003,810, Sep. 15, 1996.

[51] Int. Cl.[6] .................................................. A61M 37/00
[52] U.S. Cl. .................................................................. 604/4
[58] Field of Search .......................... 604/4–6; 210/646, 210/645, 781, 782

[56] References Cited

U.S. PATENT DOCUMENTS

| | | | |
|---|---|---|---|
| 3,710,454 | 1/1973 | Mellor | 35/17 |
| 4,436,620 | 3/1984 | Bellotti et al. | 210/90 |
| 4,530,647 | 7/1985 | Uno . | |
| 4,545,744 | 10/1985 | Weber et al. . | |
| 4,599,055 | 7/1986 | Dykstra | 417/477 |
| 4,666,598 | 5/1987 | Heath et al. | 210/239 |
| 4,676,467 | 6/1987 | Palsulich | 248/221.3 |
| 4,798,090 | 1/1989 | Heath et al. . | |
| 4,909,713 | 3/1990 | Finsterwald et al. | 417/477 |
| 5,110,270 | 5/1992 | Morrick . | |
| 5,263,831 | 11/1993 | Kappus . | |
| 5,380,173 | 1/1995 | Hellstrom . | |
| 5,484,239 | 1/1996 | Chapman et al. | 417/477 |

FOREIGN PATENT DOCUMENTS

2458694  1/1981  France .

*Primary Examiner*—John G. Weiss
*Assistant Examiner*—Ki Yong O
*Attorney, Agent, or Firm*—John R. Ley

[57] ABSTRACT

A pivotable cover secures a pump header or tubing to a peristaltic pump of a dialysis machine. The cover includes an integral raceway for engaging the pump header as a rotor of the peristaltic pump rotates along the integral raceway. The cover is pivoted away from the dialysis machine to separate the raceway from the rotor and provide substantial access for loading the pump header about the rotor. The cover is then closed to secure the pump header in place and properly position the integral raceway in relation to the pump rotor. If the pump header is connected to a blood tubing set, the cover also secures the blood tubing set in position against the dialysis machine. A detachable hinge connects the cover to the dialysis machine to allow the cover to be completely detached from the dialysis machine. The detachable cover provides complete access for cleaning the area surrounding the peristaltic pump rotor and the location where the blood tubing set is located.

30 Claims, 7 Drawing Sheets

TECHNIQUE FOR LOADING A PUMP HEADER WITHIN A PERISTALTIC PUMP OF A DIALYSIS MACHINE

CROSS-REFERENCE TO CO-PENDING PROVISIONAL APPLICATION

Priority benefits are claimed under 35 U.S.C. § 119(e) of United States Provisional Patent Application Ser. No. 60/003,810, filed Sep. 15, 1996.

FIELD OF THE INVENTION

This invention relates generally to a new and improved dialysis machine, and more particularly to a new and improved peristaltic pump used in the dialysis machine to convey blood between a patient and the machine. Even more particularly, the present invention pertains to a combination door cover and raceway for the peristaltic pump which allows a blood pump header or tubing to be more conveniently loaded into the pump during setup of the machine for dialysis treatments.

BACKGROUND OF THE INVENTION

In general, a dialysis machine is used as a substitute for the natural kidney functions of a human body. As such, the dialysis machine cleans the blood of the natural accumulation of bodily wastes and excess fluid by separating the wastes from the blood outside the body or extracorporeally. The separated wastes are discharged and the cleansed blood is returned to the body.

A dialysis machine uses a dialyzer to separate the wastes and fluid from the blood. The dialyzer includes a porous medium located within an enclosure which separates the dialyzer into a blood compartment and a dialysate compartment. The blood removed from the patient flows through the blood compartment, and a prepared solution of dialysate flows through the dialysate compartment. The wastes and fluid from the blood pass through the medium by osmosis, ionic transfer or fluid transport into the dialysate, and depending upon the type of dialysis treatment, desirable components from the dialysate may pass in the opposite direction through the medium into the blood. The transfer of the wastes and fluid from the blood into the dialysate cleanses the blood while allowing the desired components from the dialysate to enter the bloodstream.

Accomplishing these functions requires a number of complex systems and components. In an extracorporeal flow path, which conducts blood from the patient to the dialyzer and then back to the patient, at least one arterial blood pump and optionally a venous blood pump move the blood and assist in performing certain types of dialysis treatments such as ultrafiltration. Peristaltic pumps are generally used as the arterial and venous blood pumps. Peristaltic pumps offer an advantage in that blood may be effectively transferred through the extracorporeal path without being contacted by a pump mechanism such as an impeller. A peristaltic pump includes a rotor which presses a flexible pump header or tubing against a stationary raceway. By pressing or pinching the flexible pump header against the stationary raceway, a quantity of blood is trapped and pushed in front of the rotor as it rotates along the stationary raceway.

Peristaltic pumps offer a number of advantages in dialysis machines. Since the flexible pump header confines the blood, the patient's blood is not required to come into contact with surfaces which are difficult or impossible to adequately clean and disinfect. Additionally, since the flexible pump header is a part of a disposable blood tubing set used in dialysis machines, and all of the patient's blood is confined to the dialyzer and the blood tubing set, sterilization is easily accomplished and effectively maintained throughout a dialysis procedure. Furthermore a peristaltic pump applies relatively gentle motion to the blood, as compared to the more vigorous motion of an impeller pump, and thus the potential to damage the blood is reduced with peristaltic pumps. Another advantage is that the quantity of blood flow through the pump depends primarily on the size of the pump header and the rotational rate of the pump rotor. Many other advantages of peristaltic pumps are known in the field of dialysis.

A disadvantage of peristaltic pumps is the difficulty of positioning the pump header between the rotor and the raceway before using the pump. The tolerances between the rotor and the raceway are sufficiently small to ensure that the pump header is pinched closed by the rotor pressure against the raceway. The close proximity of the rotor and raceway creates difficulties in fitting the pump header between the rotor and the raceway. Furthermore the position of the rotor and raceway relative to the remaining portion of the blood tubing set typically limits the space and accessibility for loading the pump header.

To alleviate some of the time consumed and difficulty involved in loading the pump header, a variety of mechanized loading devices have been incorporated in dialysis machines. One of the more complex loading mechanisms moves the rotor and the raceway axially with respect to one another to provide space for loading the pump header. The mechanism to accomplish such movements is somewhat difficult for the operator to use, has a complexity which increases the possibilities of mechanical failure or malfunction, and often does not provide adequate convenience and accessibility for the operator to insert the pump header.

Another approach previously used with dialysis machines to facilitate loading the pump header has been to move the raceway laterally away from the rotor. Although this provides additional space between the rotor and the raceway, there is frequently inadequate space for the operator to grip the pump header and stretch it over the rotor. Another approach used in the past has been to pivotably connect a portion of the raceway so the portion can be pivoted away from the rotor in a motion within a plane in which the rotor rotates. Pivoting only a portion of the raceway frequently does not provide sufficient space to constitute a material improvement in loading the pump header. Furthermore, many of the problems associated with the lateral movement of the entire raceway are also present when only a portion of the raceway is pivoted.

Most of the problems involved in loading the pump header or tubing are also replicated when the blood tubing set must be removed from the machine after treatment. An additional disadvantage of the prior mechanisms is that their complex structure and numerous parts makes cleaning them very difficult during the periodic cleaning of the dialysis machine.

It is with respect to the problems of loading the pump header or tubing of a blood tubing set on a peristaltic pump in a dialysis machine, and the relatively inadequate prior attempts to solve these problems, that this invention has evolved.

SUMMARY OF THE INVENTION

A significant aspect of the present invention relates to allowing operators of dialysis machines to quickly and conveniently load a pump header or tubing of a blood tubing set into a peristaltic pump. Another significant aspect of the present invention pertains to providing more than adequate access space surrounding a rotor of a peristaltic pump in which to load a pump header. A further significant aspect of the present invention relates to completely eliminating the constraint of a raceway surrounding the rotor to obtain more access space for loading a pump header in a peristaltic pump. Another significant aspect of the present invention relates to providing a single detachable cover for simultaneously holding a blood tubing set in place against a dialysis machine and providing a raceway for operating a peristaltic blood pump. A still further significant aspect of the present invention pertains to facilitating the ability to clean peristaltic blood pumps in dialysis machines after treatment. Another important aspect relates to attaining all of the foregoing features while preventing access to the rotating parts of the peristaltic pump and thereby shielding the moving pump parts from unintentional and potentially dangerous contact by the operator.

In accordance with these and other aspects, the present invention generally relates to a pivotable cover for securing a blood tubing set to a dialysis machine. The cover provides an integral raceway against which a pump header is contacted by a rotor of a peristaltic pump. A hinge pivotably connects the cover to a housing of the dialysis machine. The cover may be pivoted away from the machine to move the raceway away from the rotor and provide substantial access for loading the pump header around the rotor. Once the pump header is properly positioned about the rotor, the cover is closed to secure the pump header in place and position the integral raceway in proper position relative to the pump rotor.

If a blood tubing set is attached to the pump header, the blood tubing set may be properly positioned when the cover is opened and secured in place once the cover is closed. Furthermore, the hinge connecting the cover to the housing may be detached from the housing to allow the cover to be completely removed from the dialysis machine. The detachable cover provides complete access for cleaning the area surrounding the peristaltic pump rotor and the location where the blood tubing set is located.

Thus, the pivotable and detachable cover combined with an integral peristaltic pump raceway allows for easy setup of a pump header by completely removing the raceway during the procedure of fitting the pump header about the rotor of the peristaltic pump. The cover may also be beneficially used to secure a blood tubing set to a dialysis machine. Furthermore, the cover may be detached from the dialysis machine for periodic cleaning of the machine or for replacing the cover should it experience damage or excessive wear.

Many other beneficial features of the present invention, and a more complete appreciation of the present invention and its scope, may be understood from the accompanying drawings, which are briefly summarized below, from the following detailed description of a presently preferred embodiment of the invention, and from the appended claims.

DETAILED DESCRIPTION

Figure 1:
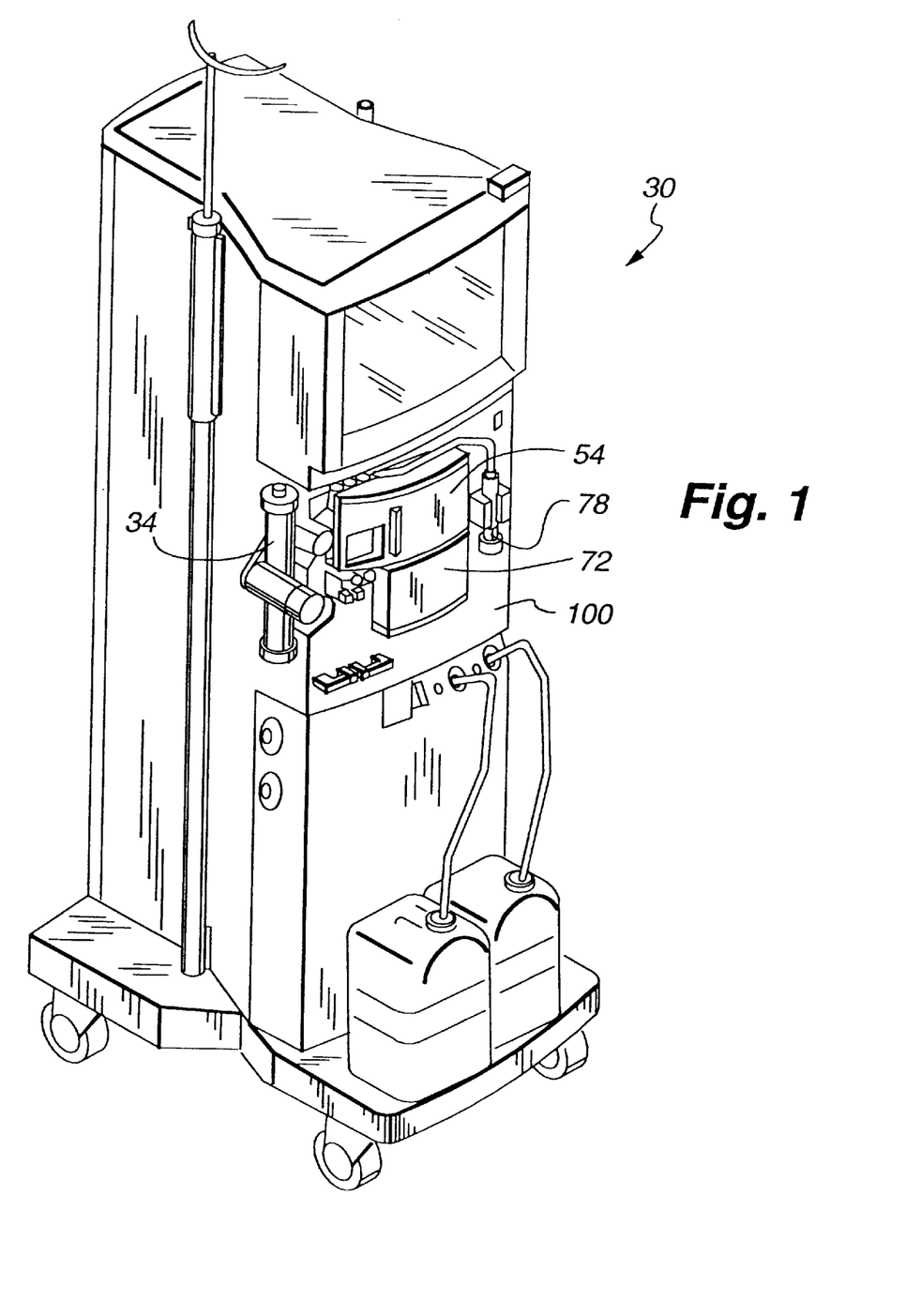
FIG. 1 is an isometric view of a dialysis machine which incorporates the present invention.

An example of a dialysis machine with which the present invention may be advantageously employed is shown at 30 in FIG. 1. The dialysis machine 30 includes the components generally shown in FIG. 2, and those components establish an extracorporeal flow path and a hydraulics flow path. The extracorporeal flow path conducts blood from a patient 32 to a dialyzer 34, and then returns the blood from the dialyzer 34 to the patient 32. The hydraulics flow path conducts dialysate from a supply 36 to the dialyzer 34, and then returns the used dialysate to a waste drain 38. In actual practice, the dialysate supply 36 preferably includes a supply of chemicals and water continuously mixed by the dialysis machine 30, and the waste drain 38 is typically a public sewer.

Figure 2:
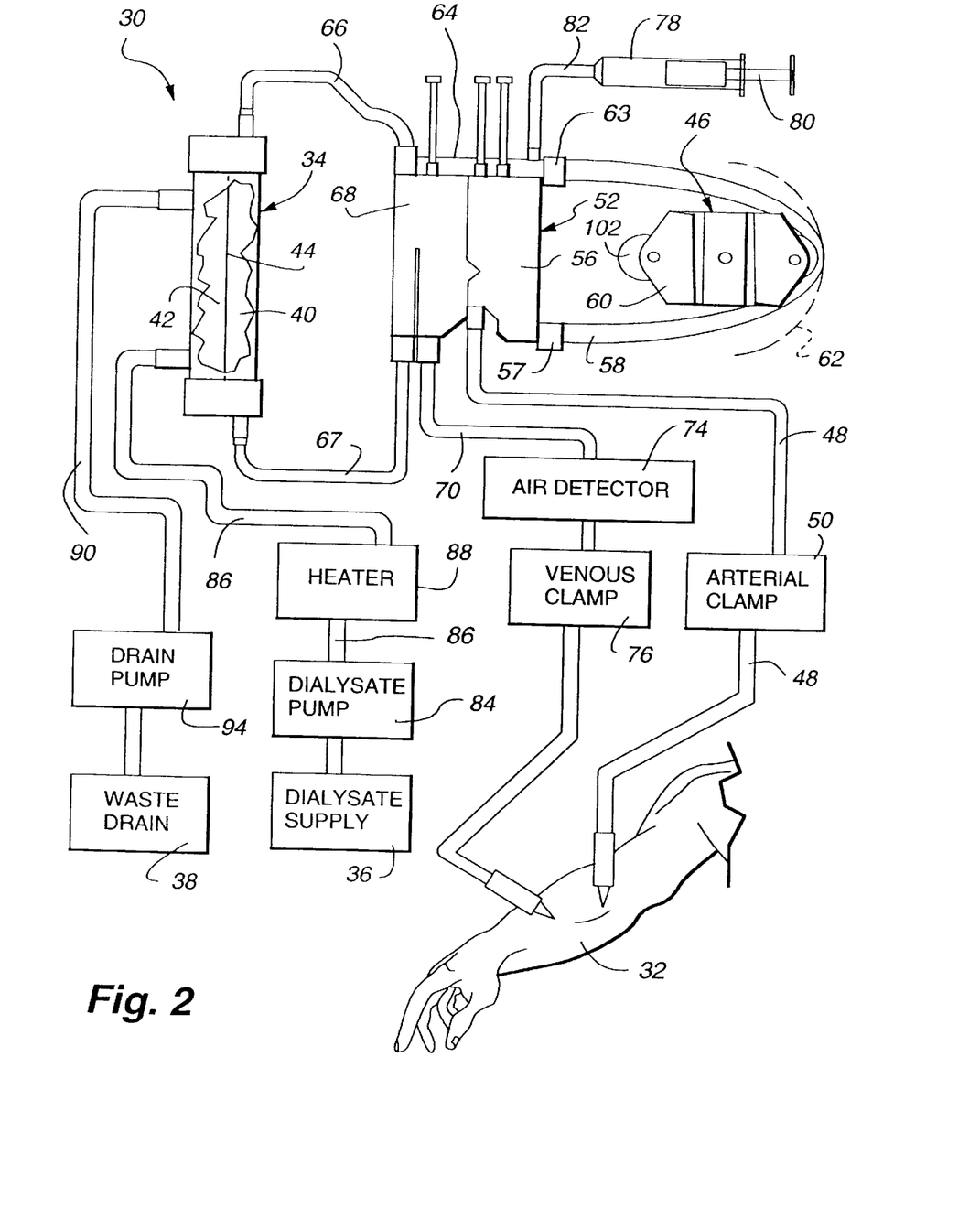
FIG. 2 is a generalized view illustrating a dialyzer, an extracorporeal blood flow path (including a peristaltic pump) from a patient through the dialyzer, and a hydraulics flow path for dialysate through the dialyzer, as are present during treatment of a patient with the dialysis machine shown in FIG. 1.

The blood in the dialyzer 34 is confined to a blood chamber 40, and the dialysate in the dialyzer 34 is confined to a dialysate chamber 42. The blood chamber 40 and the dialysate chamber 42 are separated by a microporous or other type of dialysis medium 44. The waste products contained in the blood within the blood chamber 40 are transferred through the medium 44 by osmosis, ionic transfer or flow transfer to the dialysate in the dialysate chamber 42. Desirable components of the dialysate in the dialysate chamber 42 may also be transferred to the blood in the blood chamber 40 by the same mechanisms. In this manner, the waste products are removed from the patient's blood, and the cleansed blood is returned to the patient 32. The used dialysate flowing from the dialysate chamber 42 discharges the waste products into the drain 38.

The elements of the extracorporeal flow path include at least one blood pump 46 which controls the flow of blood through the extracorporeal path. The blood pump 46 is preferably a peristaltic pump in dialysis machines. An arterial line or tubing 48 extends from the patient 32 through an arterial clamp 50 to a blood tubing set or handling cartridge 52. Since the blood handling cartridge 52 is normally retained behind a cover or door 54 (FIG. 1) of the machine 30 when used, it is not shown in FIG. 1. The blood pump 46 is also located behind the door 54 adjacent to the cartridge 52.

Blood flows through the arterial line 48 and into an arterial chamber 56 of the cartridge 52. The blood pump 46 draws blood from an outlet 57 of the arterial chamber 56 through a pump header or tubing 58 which is squeezed or pinched by a rotating rotor 60 against a stationary raceway 62, in the typical manner of peristaltic pumps. The blood within the pump header 58 which is rotationally in front of the rotor 60 is propelled through the pump header 58 and into an inlet 63 of a manifold 64 of the cartridge 52. A tubing 66 conducts the blood from the manifold 64 of the cartridge 52 into the dialyzer 34.

Figure 3:
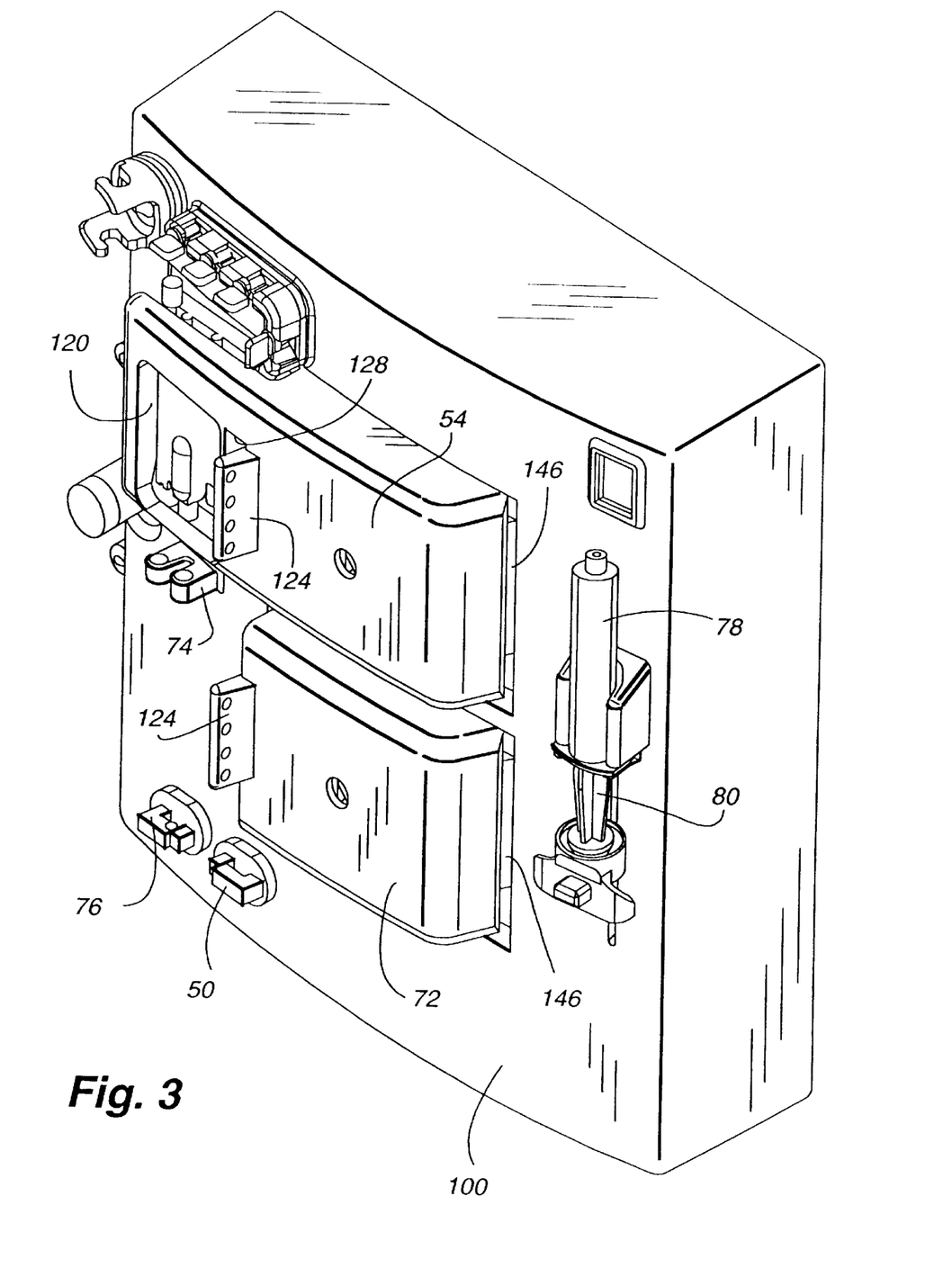
FIG. 3 is an isometric view of a center portion of the dialysis machine shown in FIG. 1 illustrating an outer panel which includes a preferred cover and mechanism of the present invention.

The cleansed blood flowing from the dialyzer 34 is transferred through a tubing 67 back to a venous chamber 68 of the cartridge 52. Blood from the venous chamber 68 is removed from the cartridge 52 through a venous tubing or line 70. Although not shown in FIG. 2, a venous blood pump similar to the arterial blood pump 46 may be located along the venous line 70 to assist in forcing the blood back into the patient 32 or to regulate the flow of blood through the extracorporeal flow path. If employed, the venous blood pump is positioned behind a second door 72 of the dialyzer machine 30, as shown in FIGS. 1 and 3.

After leaving the venous chamber 68, the blood flows through the venous line 70 to an air detector 74. The air detector 74 derives signals related to any air in the venous line 70. If an excessive or dangerous amount of air is present, a venous line clamp 76 will immediately close (and the pump 46 will stop) to terminate the flow of blood through the venous line 70 before the air reaches the patient 32.

Because the blood in the extracorporeal flow path is prone to clot, a blood anticoagulant such as heparin is injected into the extracorporeal flow path. The anticoagulant is slowly delivered from a syringe 78 as a result of a linear driver mechanism (not shown) moving a plunger 80 into the syringe 78. Anticoagulant from the syringe 78 is introduced into the arterial chamber 56 of the cartridge 52 through a tubing 82.

The elements of the hydraulics flow path include a number of different valves (most of which are not shown) and a dialysate pump 84 which draws dialysate from the supply 36. The supply 36 is typically dialysate which the dialysis machine 30 has prepared from appropriate chemicals and a supply of purified water. The dialysate pump 84 draws the dialysate from the supply 36 and delivers it through a dialysate supply tubing or line 86 and into the dialysate chamber 42 of the dialyzer 34. The dialysate flows past the medium 44 where it absorbs the waste products from the blood in the blood chamber 40. Any beneficial components within the dialysate which are desired to be transferred to the blood pass through the medium 44 and into the blood in the blood chamber 40. Prior to entering the dialyzer 34, the dialysate is heated in a heater 88 to the normal human body temperature.

The used dialysate containing the waste products is removed from the dialysate chamber 42 through a dialysate waste tubing or line 90 by operation of a drain pump 94. The dialysate containing the waste products is delivered by the drain pump 94 to the waste drain 38.

The present invention relates specifically to loading a blood tubing set or handling cartridge 52 onto a dialysis machine 30 in a manner which enhances the ease of loading a pump header or tube 58 between the rotor 60 and stationary raceway 62 of a peristaltic blood pump 46. Although shown primarily in relation to the arterial blood pump 46, the features of the present invention may also be used in conjunction with a similar venous blood pump if such a pump is employed on the dialysis machine. The details of the invention are applicable to many peristaltic pump applications.

Figure 4:
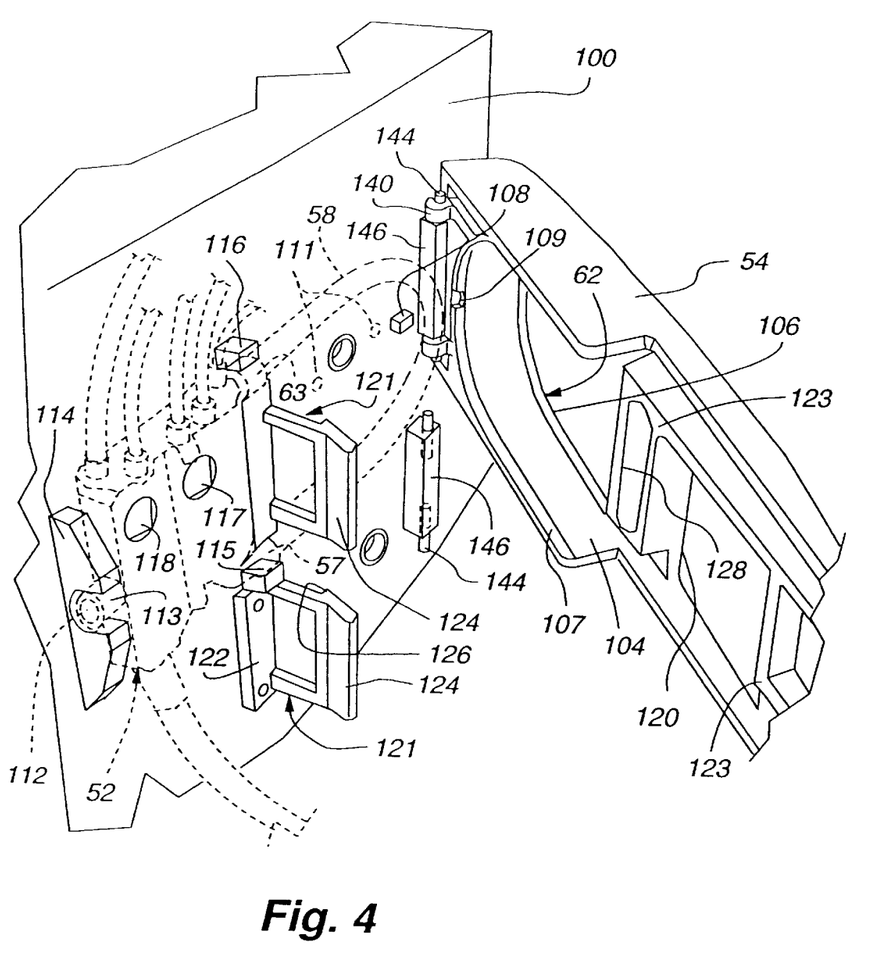
FIG. 4 is an isometric view of the center portion shown in FIG. 3, illustrating the preferred cover of the present invention with the location of a blood tubing set shown in phantom and the details of the peristaltic pump omitted for clarity.

The preferred details of the blood pump 46 are generally shown in FIGS. 3–6. One end of the cover 54 includes a hinge pivotably connected to an exterior surface 100 of the dialysis machine 30. The cover 54 also defines an integral raceway 62 having the typical semi-circular shape of peristaltic pump raceways, with the closed end of the semi-circle positioned adjacent the hinged end of the cover 54 (FIG. 4). The cover 54 is preferably molded from a sturdy plastic material, such as polycarbonate, to provide the complex shape of the integral raceway 62.

Figure 5:
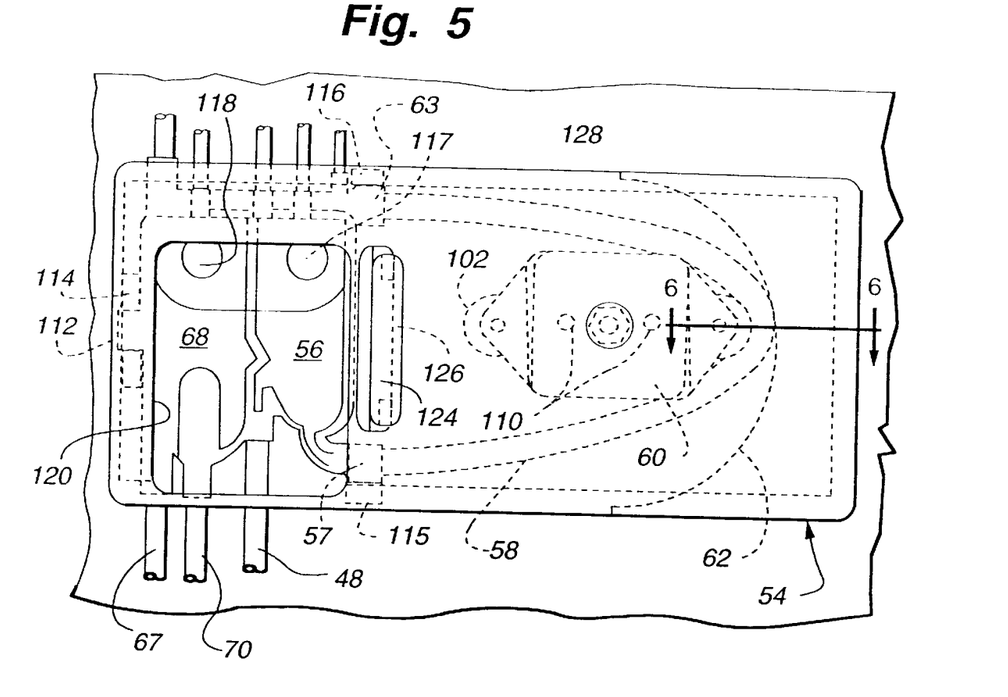
FIG. 5 is a partial front elevational view of the center portion shown in FIG. 3, illustrating the peristaltic blood pump (shown in phantom) and a blood tubing set (partially shown in phantom) secured into place by the preferred cover of the present invention.
Figure 6:
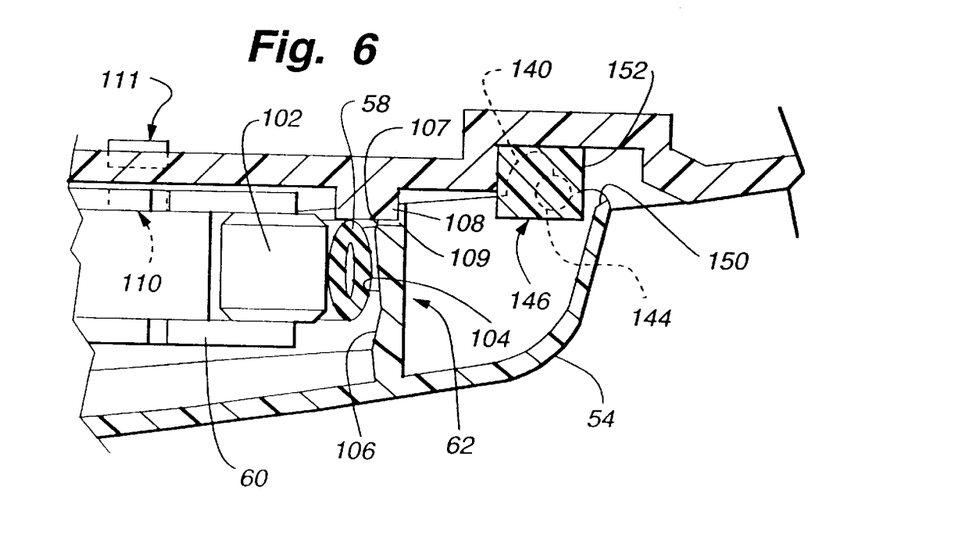
FIG. 6 is an enlarged, partial section view of the cover, peristaltic pump and blood tubing set, taken substantially along the line 6—6 in FIG. 5.

The hinged connection allows the cover 54 to pivot away from the housing 100 to provide access to the rotor 60 (FIG. 5) of the pump 46. The rotor 60 includes rollers 102 at the outer radial ends of the rotor 60 for contacting the pump header 58 and squeezing the header tubing against the raceway 62 during operation of the pump 46 (FIGS. 5 and 6). The blood trapped in front of the location where the roller 102 pinches the header 58 is pushed forward along the header by the rotating rotor in the above-described manner.

The integral raceway 62 includes a main contact surface 104 which faces substantially perpendicular to the surface of the roller 102 when the cover 54 is closed (FIG. 6). The raceway 62 also includes two beveled edges 106 and 107, one on either side of the main contact surface 104, as shown in FIGS. 4 and 6. The exterior edge 106 is beveled toward the roller 102 to help center and contain the header 58 of the blood handling cartridge 52. However, the interior edge 107 is beveled away from the roller 102 to prevent the edge 107 from binding on the header 58 as the cover 54 is closed. To further ensure that the header 58 will not bind when the cover 54 is closed, a projection 108 (FIGS. 4, 6 and 12) extends away from the exterior surface 100 of the dialysis machine at a position adjacent the header 58 once the header is loaded around the roller 102. The projection 108 is thus in a position (best shown in FIG. 6) to contact the pump header 58 and prevent the header from being pushed off the roller 102 and pinched by the cover 54 should the raceway 62 tend to contact the header 58 as the cover 54 is closed. A notch 109 (FIGS. 4, 6 and 12) formed in the interior edge 107 of the raceway 62 accommodates the projection 108 when the cover 54 is closed. Thus, the interior beveled edge 107 and the projection 108 enhance the ease of closing the cover 54 and the integrated raceway 62 once the header 58 has been loaded about the rotor 60 of the pump 46.

The integration of the raceway 62 within the hinged cover 54 provides substantially unimpeded access to the pump rotor 60 and the surrounding area for loading the pump header 58 when the cover 54 is in the open position (FIG. 4).

The hinged end of the cover 54 is laterally spaced from the semi-circular raceway 62 to ensure that no part of the cover 54 or the integrated raceway 62 interferes with the procedure of loading the pump header 58 about the rotor 60 when the cover 54 is open and pivoted away from the housing 100 (FIG. 4).

The pump header 58 is preferably placed around the rotor 60 when the rotor is oriented in a horizontal position, as shown in FIG. 5. In this manner, the cover 54 (and the integrated raceway 62) may be closed about the rotor 60 and the header 58 to secure the blood handling cartridge 52 in place. When the cover 54 is closed, the closed end of the semi-circular raceway 62 will contact the header 58 opposite the roller 102, as shown in FIG. 5.

To ensure that the rotor 60 is in the preferred horizontal position for loading the header 58, a microcontroller (not shown) operates the pump 46 at the start-up of the dialysis machine 30 to rotate the rotor to a horizontal position. Magnets 110 placed within each end of the rotor 60 adjacent the rollers 102 may be used in conjunction with a separate magnet or magnetic sensor 111 within the housing 100 (FIG. 6) to indicate to the microcontroller when the rotor is in a horizontal position and thus when to halt the operation of the pump 46. For example, the microcontroller will rotate the pump rotor in a predetermined direction (e.g. clockwise as shown in FIG. 5) when the dialysis machine 30 is initially turned on or powered up from a low-power mode. The magnetic sensor 111 is positioned within the housing 100 so that the magnets 110 within the ends of the rotor pass by the sensor 111 when the rotor is in a substantially horizontal position. The microcontroller will then halt the pump 46 when it senses that one of the magnets 110 is aligned with the magnetic sensor 111. Additionally, the microcontroller may use the magnets 110 and the sensor 111 to verify that the pump 46 is operating properly and to establish the speed of the pump 46 during the dialysis treatment.

Figure 11:
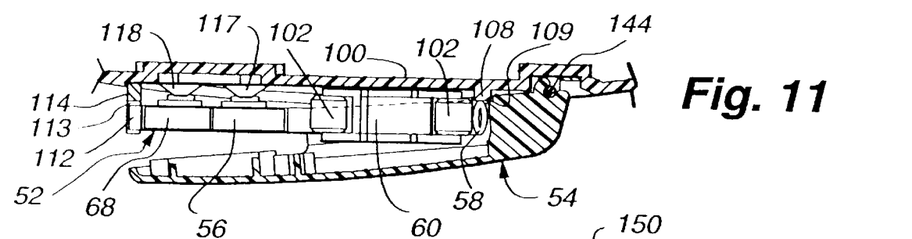
FIG. 11 is a section view of the cover similar to FIG. 6, illustrating a blood tubing set being secured into position adjacent the peristaltic pump.

The hinged cover 54 is of a length which causes it to also hold the remainder of the blood handling cartridge 52 in place at a location adjacent to the rotor 60 (FIGS. 5 and 11). Once the cover 54 is in the open position, a blood handling cartridge 52 may be positioned on the dialysis machine as shown in FIG. 4. A round pin 112 (FIG. 4) protrudes from the venous chamber 68 of the cartridge 52 and mates with a slot 113 defined within a clip 114 extending from a left side of the housing 100. The arterial chamber outlet 57 and the manifold inlet 63 of the cartridge 52 are preferably retained between two protrusions 115 and 116, respectively, to hold the right side of the cartridge 52 in place on the dialysis machine, as shown in FIG. 4. Thus, the blood handling cartridge 52 is temporarily held in position by the clip 114 and the protrusions 115 and 116 while the cover 54 is in the open position and the pump header 58 is fitted about the horizontal rotor 60.

Figure 7:
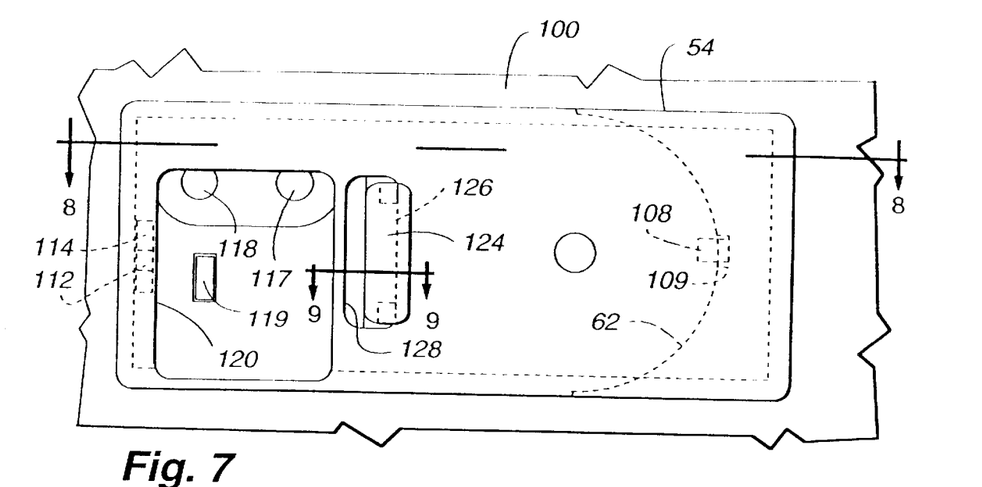
FIG. 7 is a partial front elevational view of the cover similar to FIG. 5, with the blood tubing set and peristaltic blood pump omitted for clarity.

Additionally, the preferred embodiment of the blood handling cartridge includes pressure pods on the rear of the arterial and venous chambers 56 and 68. These pressure pods communicate with pressure sensors 117 and 118 within the housing 100 for measuring blood pressure levels within the arterial and venous chambers 56 and 68, respectively. Details of the pressure pods formed within the arterial and venous chambers 56 and 68, as well as the pressure sensors 117 and 118, may be found in U.S. Pat. No. 4,676,467, assigned to the assignee hereof. Once the pump header 58 has been loaded about the rotor 60, and the pressure pods on the arterial and venous chamber 56 and 68 have been aligned with their respective pressure sensors 117 and 118, the cover 54 may be closed to maintain the position of the blood handling cartridge 52 during the dialysis treatment. An end of the cover 54 opposite the integrated raceway 62 includes contact surfaces 123 (FIG. 4) for engaging the rigid components of the blood handling cartridge (e.g., the arterial and venous chambers 56 and 68) when the cover 54 is in the closed position. The contact surfaces 123 of the cover 54 maintain the pin 112 within the slot 113 of the clip 114 and, together with the protrusions 115 and 116, hold the cartridge 52 in proper position relative to the housing 100. A bumper 119 (FIGS. 7 and 8) mounted on the housing 100 of the dialysis machine contacts a rear surface of the blood handling cartridge 52 to restrain a lower portion of the cartridge and prevent it from moving relative to the dialysis machine.

The preferred embodiment of the cover 54 defines an opening 120 (FIGS. 3, 4, 5 and 7) which provides access and an unobstructed view of the arterial and venous chambers 56 and 68 when the cover 54 is closed over the blood handling cartridge 52.

Figure 9:
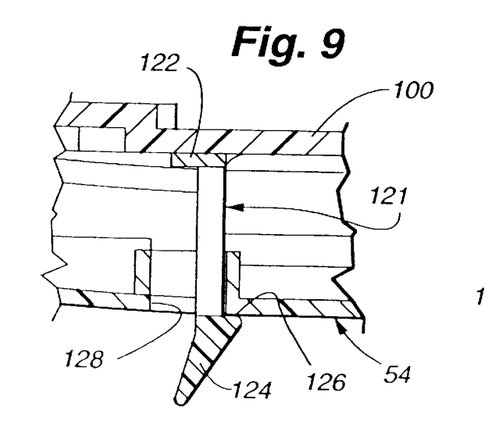
FIG. 9 is an enlarged, partial section view taken substantially along the line 9—9 in FIG. 7.

The cover 54 is preferably held in the closed position by a resilient latch member 121. An inner end 122 of the latch member 121 is attached to the housing 100 (FIGS. 4 and 9). An outer end of the latch member is shaped in the form of a hook 124 having a depending flange 126, as shown in FIGS. 4 and 9. The hook 124 extends through an opening 128 (FIG. 7) defined in the cover 54 when the cover is in the closed position, and the depending flange 126 on the hook 124 engages an outer surface of the cover 54 at a corner of the opening 128 to maintain the cover in the closed position. When it is desired to open the cover 54, the outer hook 124 of the resilient latch member 121 is bent slightly (to the left as shown in FIG. 9) to disengage the flange 126 from the corner of the cover 54 and release the contact of the hook 124 with the outer surface of the cover. Once the hook 124 is disengaged, the cover 54 is free to pivot away from the housing 100 for loading and unloading the blood tubing set or handling cartridge 52.

Figure 8:
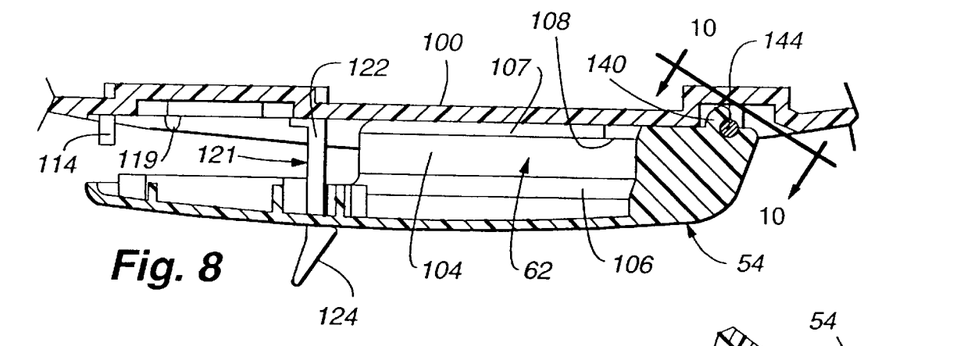
FIG. 8 is a section view taken substantially along the line 8—8 in FIG. 7.
Figure 10:
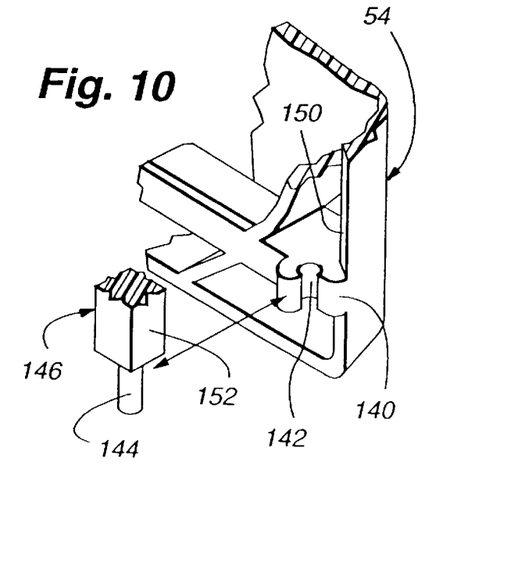
FIG. 10 is an isometric view of details of a hinge and a beveled edge of the preferred cover of the present invention, taken substantially along point-of-view line 10—10 in FIG. 8.

The hinged end of the cover 54 is connected to the housing 100 by hooks 140 which extend from the end of the cover as best shown in FIGS. 4, 8 and 10. Each hook 140 includes an inward extending slot 142 (FIG. 10). The slot 142 is adapted to receive a hinge pin 144 which is connected to the housing 100 by a retaining block 146. The retaining block 146 preferably includes a hinge pin 144 at its top and bottom ends, as shown in FIG. 4, to prevent longitudinal movement of the cover 54 relative to the retaining block 146. Alternatively, a single hinge pin 144 could extend through the entire length of the retaining block 146.

Figure 12:
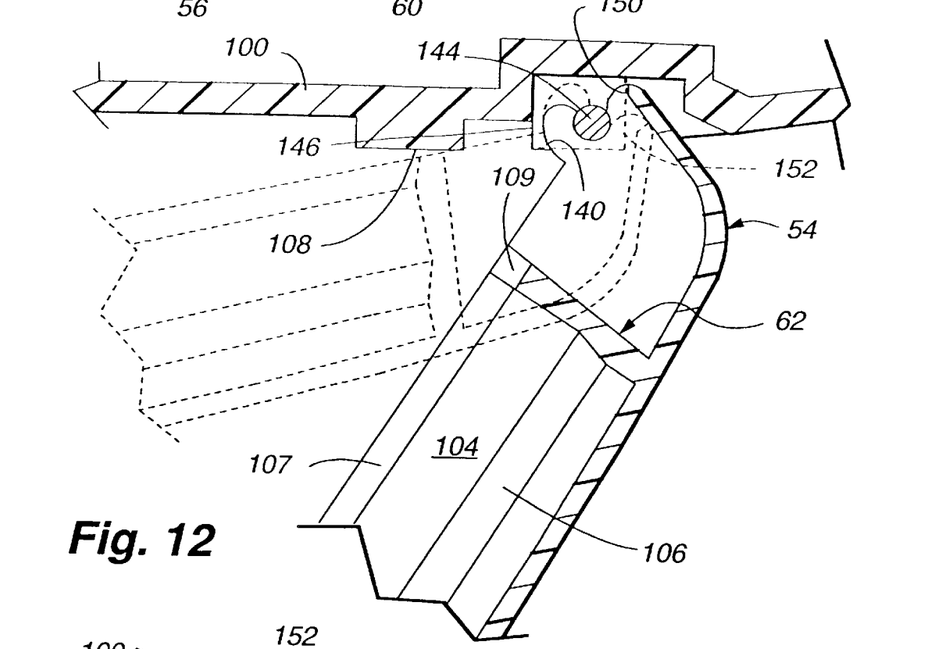
FIG. 12 is an enlarged, partial section view of the cover similar to FIG. 6, illustrating the cover in two separate open positions, with the blood tubing set and peristaltic pump omitted for clarity.
Figure 13:
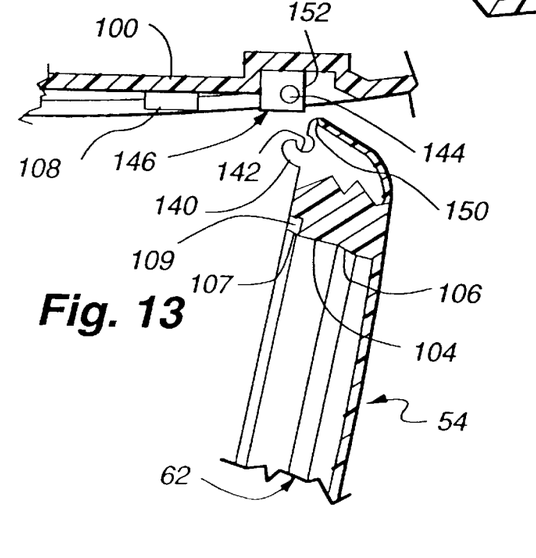
FIG. 13 is a partial section view similar to FIG. 12, illustrating the cover disengaged from the dialysis machine.

The hooks 140 are formed of the same plastic material as the remainder of the cover 54, and thus they have sufficient resilience to allow the cover 54 to be selectively detached from and reattached to the housing 100 of the dialysis machine 30 by pulling the hooks 140 off of their respective hinge pins 144 (FIG. 13). To facilitate in removing the cover 54, the hinged end of the cover includes a beveled surface 150, as best shown in FIGS. 6 and 10. The beveled surface 150 is angled so that it will contact a side surface 152 of the retaining block 146 in a substantially flush manner when the cover 54 has been pivoted open through a predetermined angle, as shown in FIG. 12. If an opening force is applied to the cover 54 after the cover has reached the predetermined angle, the force will be transmitted to the retaining block 146 by contact with the beveled surface 150, and the beveled surface 150 will act as a cam to pry the hinge pins 144 from the slots 142 of the hooks 140. The slots 142 are oriented (FIG. 12) to accommodate the outward cam force applied by the beveled surface 150 and release the hinge pins when the cover is at a maximum open position. In this manner, the cover 54 is securely attached to the housing 100 but may be easily detached by pivoting the cover beyond the predetermined opening angle defined by the beveled surface 150, as shown in FIGS. 12 and 13.

The detachable cover 54 provides the maximum available access to the area surrounding the rotor 60 and the location where the blood tubing set or handling cartridge 52 is normally retained. This maximum access allows these areas of the dialysis machine 30 to be fully cleaned during the periodic cleanings of the machine 30. The ability to fully clean the dialysis machine is a further advantage of the present invention in relation to the relatively complex (and fixed) types of pump header loading mechanisms. Additionally, the cover may be easily and quickly replaced if it should be broken or if a different type of raceway is desired (e.g., if a different size rotor and pump header are used).

When the dialysis machine 30 includes a venous blood pump (not shown), the cover 72 (FIGS. 1 and 3) is substantially identical to the cover 54, except that the cover 72 is shorter in length than the cover 54. Similarly, the cover 72 includes a latch member 121 and retaining block 146, as shown in FIG. 4. The reduced length of the cover 72 is due to the fact that it need only provide a stationary raceway 62 for the second blood pump and it is not required to hold a separate blood tubing set or handling cartridge 52 (as is required of the cover 54). Because of its reduced length, the end of the cover 74 opposite the hinged end interacts directly with the hook 124 of the resilient latch member 121 to hold the cover 74 closed.

Although the cover 54 includes the opening 120 for viewing the blood handling cartridge, the covers 54 and 72 are preferably made from a transparent plastic to allow a dialysis machine operator to view the operation of the blood pumps and the position of the pump headers within the integral raceways when the covers 54 and 72 are closed.

In summary, the single cover 54 allows easy access for loading and removing the entire blood tubing set or handling cartridge 52. Additionally, the integration of the raceway 62 with the cover 54 of the present invention allows substantially improved access to the rotor of a peristaltic pump for loading the pump header of the blood handling cartridge. Furthermore, the easily detachable nature of the cover allows the area surrounding the rotor and the location where the blood handling cartridge is positioned to be thoroughly cleaned.

A presently preferred embodiment of the present invention and many of its improvements have been described with a degree of particularity. This description is a preferred example of implementing the invention, and is not necessarily intended to limit the scope of the invention. The scope of the invention is defined by the following claims.

What is claimed is:

1. In a dialysis machine having a hydraulic flow path for delivering dialysate to a dialyzer, peristaltic blood pump with a rotor for controlling a flow of blood through an extracorporeal flow path which includes the dialyzer, the extracorporeal flow path including a flexible pump header which the rotor pinches during rotation to pump blood in the extracorporeal flow path, and an improved cover for securing the pump header relative to the rotor for blood pumping, said cover comprising:

a hinge pivotably connecting one end of the cover to the dialysis machine to allow the cover to pivot between a closed position wherein the pump header is pinched by the rotor for blood pumping and an open position extended away from the dialysis machine wherein the pump header is not pinched for blood pumping; and an integral raceway of the cover for engaging the flexible pump header to allow the rotor to pinch the pump header against the raceway during blood pumping, said raceway engaging the flexible pump header for blood pumping only when the cover is pivoted to the closed position; and wherein:

said hinge allows selective detachment of the cover from the dialysis machine.

2. In a dialysis machine as defined in claim 1, said integral raceway includes an interior edge beveled away from the rotor when the cover is in the closed position.

3. In a dialysis machine as defined in claim 2, said integral raceway includes an exterior edge beveled toward the rotor when the cover is in the closed position.

4. In a dialysis machine as defined in claim 3, the cover and the integral raceway are molded as a single plastic part.

5. In a dialysis machine having a hydraulic flow path for delivering dialysate to a dialyzer, a peristaltic blood pump with a rotor for controlling a flow of blood through a blood tubing set connected in an extracorporeal blood flow path which also includes the dialyzer, the blood tubing set including a cartridge and a flexible pump header extending from the cartridge, the rotor pinching the pump header during rotation to pump blood in the extracorporeal flow path, and an improved cover for securing the cartridge to the dialysis machine and the pump header relative to the rotor for blood pumping, said cover comprising:

a hinge pivotably connecting one end of the cover to the dialysis machine to allow the cover to pivot between a closed position wherein the cartridge is held in position and the pump header is pinched by the rotor for blood pumping and an open position extended away from the dialysis machine wherein the cartridge is exposed and the pump header is not pinched for blood pumping;

an integral raceway of the cover for engaging the flexible pump header to allow the rotor to pinch the pump header against the raceway during blood pumping, said raceway engaging the flexible pump header for blood pumping only when the cover is pivoted to the closed position; and at least one cartridge contact surface of the cover to contact the cartridge and secure the blood tubing set to the dialysis machine for blood pumping when the cover is pivoted to the closed position.

6. In a dialysis machine as defined in claim 5, said cover may be pivoted to the closed position to engage the raceway with the flexible pump header substantially only when the rotor is in a predetermined position.

7. In a dialysis machine as defined in claim 6, said raceway includes an interior edge beveled away from the rotor when the cover is in the closed position.

8. In a dialysis machine as defined in claim 7, said raceway includes an exterior edge beveled toward the rotor when the cover is in the closed position.

9. In a dialysis machine as defined in claim 8, the cover and the raceway are molded as a single plastic part.

10. In a dialysis machine as defined in claim 5, said cover is selectively attachable to and detachable from the dialysis machine.

11. In a dialysis machine as defined in claim 10:

the one end of the cover pivotably connected to the dialysis machine includes a beveled surface adapted to contact the dialysis machine and apply a force to detach the cover from the dialysis machine when the cover is pivoted beyond a predetermined angle in the open position.

12. In a dialysis machine as defined in claim 11, the cover and the raceway are molded as a single plastic part.

13. In a dialysis machine as defined in claim 5, wherein the cover further includes:
an opening to provide an unobstructed view of a portion of the blood tubing set when the cover is pivoted to the closed position and the blood tubing set is secured to the dialysis machine.

14. A dialysis machine having a hydraulic flow path for delivering dialysate to a dialyzer through which blood is also Pumped in an extracorporeal blood flow path, said dialysis machine comprising:
a peristaltic blood pump having a rotor to engage a flexible pump header of a blood tubing set within the extracorporeal blood flow path; and
a cover pivotably attached to the dialysis machine, said cover including at least one contact surface to secure the blood tubing set to the dialysis machine, and said cover further defining an integral raceway for engaging the flexible pump header to allow the rotor to pinch the pump header against the integral raceway as the rotor rotates along the integral raceway to pump blood through the flexible pump header and the extracorporeal blood flow path.

15. A dialysis machine as defined in claim 14, wherein:
the cover pivots between a closed position an open position extended away from the dialysis machine;
the cover secures the blood tubing set to the dialysis machine only when the cover is pivoted to the closed position; and
the raceway substantially engages the pump header for blood pumping only when the cover is pivoted to the closed position.

16. A dialysis machine as defined in claim 15, wherein said raceway includes an interior edge beveled away from the rotor when the cover is in the closed position.

17. A dialysis machine as defined in claim 16, wherein said raceway includes an exterior edge beveled toward the rotor when the cover is in the closed position.

18. A dialysis machine as defined in claim 17, wherein the cover and the integral raceway are molded as a single plastic part.

19. A dialysis machine as defined in claim 15, wherein said cover further comprises:
a hinge connected to one end of the cover and operative to selectively attach and detach the cover from the dialysis machine.

20. A dialysis machine as defined in claim 19, wherein:
the one end of the cover pivotably attached to the dialysis machine includes a beveled surface adapted to contact the dialysis machine and apply a force to detach the hinge from the dialysis machine when the cover is pivoted beyond a predetermined angle in the open position.

21. A dialysis machine as defined in claim 20, wherein the cover and the integral raceway are molded as a single plastic part.

22. A dialysis machine as defined in claim 15, wherein the cover may be pivoted to the closed position to engage the raceway with the pump header substantially only when the rotor is in a predetermined position.

23. A dialysis machine as defined in claim 15, wherein:
the cover defines an opening to provide an unobstructed view of a portion of the blood tubing set when the cover is pivoted to the closed position and the blood tubing set is secured to the dialysis machine.

24. A dialysis machine as defined in claim 14, wherein:
the dialysis machine includes a venous pressure sensor and an arterial pressure sensor; and the blood tubing set further comprises:
a rigid venous chamber having a pressure pod adapted to engage the venous pressure sensor of the dialysis machine; and
a rigid arterial chamber having a pressure pod adapted to engage the arterial pressure sensor of the dialysis machine.

25. A dialysis machine as defined in claim 24, wherein:
the dialysis machine further includes a slot; and the blood tubing set further comprises:
a pin fixed to the rigid venous chamber, said pin adapted to engage the slot on the dialysis machine to fix the position of the blood tubing set in relation to the dialysis machine.

26. A dialysis machine having a hydraulic flow path for delivering dialysate to a dialyzer through which blood is also pumped in an extracorporeal blood flow path, said dialysis machine comprising:
a peristaltic blood pump having a rotor to engage a flexible pump header of a blood tubing set within the extracorporeal blood flow path;
a cover pivotably attached to the dialysis machine, said cover including at least one contact surface to secure the blood tubing set to the dialysis machine, and said cover further defining an integral raceway for engaging the flexible pump header to allow the rotor to pinch the pump header against the integral raceway as the rotor rotates along the integral raceway to pump blood through the pump header and the extracorporeal blood flow path, the cover pivoting between a closed position and an open position extending away from the dialysis machine, the cover securing the blood tubing set to the dialysis machine when the cover is Pivoted to the closed position, the raceway engaging the pump header for blood pumping when the cover is pivoted to the closed position, and the cover pivoting to the closed position only when the rotor is in a predetermined position;
a magnet attached to the rotor;
a magnetic sensor positioned relative to the blood pump to align with the magnet when the rotor is substantially in the predetermined position; and
a microprocessor to sense when the magnet and the magnetic sensor are aligned.

27. A dialysis machine as defined in claim 26, wherein the microprocessor is adapted to rotate the rotor and align the magnet with the magnetic sensor to position the rotor in the predetermined position when the cover is pivoted to the open position.

28. A dialysis machine as defined in claim 26, wherein said cover further comprises:
a hinge to selectively attach the cover to and detach the cover from the dialysis machine.

29. A dialysis machine as defined in claim 28 wherein:
an end of the cover is pivotably attached to the dialysis machine and includes a beveled surface adapted to contact the dialysis machine and apply a force to detach the cover from the dialysis machine when the cover is pivoted beyond a predetermined angle in the open position.

30. A dialysis machine as defined in claim 29 wherein the cover and the integral raceway are molded as a single plastic part.

* * * * *